United States Patent [19]
Pohl et al.

[11] Patent Number: 5,314,426
[45] Date of Patent: May 24, 1994

[54] EXTERNAL BONE FIXATION DEVICE

[76] Inventors: Anthony P. Pohl, 8 Caralue Road, Marino, Australia, 5049; Bruce H. Ide, 7 Orchard Court, Newton, Australia, 5074

[21] Appl. No.: 48,405

[22] Filed: Apr. 14, 1993

[30] Foreign Application Priority Data

Apr. 16, 1992 [AU] Australia ............... PL1971

[51] Int. Cl.$^5$ ............................................... A61B 17/60
[52] U.S. Cl. ........................................ 606/58; 606/59
[58] Field of Search ............ 606/53, 54, 55, 57, 606/58, 105, 59

[56] References Cited

U.S. PATENT DOCUMENTS

| | | | |
|---|---|---|---|
| 2,024,325 | 12/1935 | Allen | 606/54 |
| 2,056,749 | 10/1936 | Thomas | 606/54 |
| 4,475,546 | 10/1984 | Patton | 606/57 |

FOREIGN PATENT DOCUMENTS 37856 1/1955 Poland ............... 606/54

*Primary Examiner*—Tamara L. Graysay
*Attorney, Agent, or Firm*—Townsend & Townsend Khourie and Crew

[57] ABSTRACT

The invention relates to a unilateral external bone fixation device which can be readily adapted for carrying out either bone transport or bone lengthening procedures, the device comprising a non-rotatable rigid shaft 11 having a central bore 12 extending therethrough, and being longitudinally displaceable along the central axis of the device, and a plurality of clamp carrier housings 13, 14 15 co-axially supported along the length of the shaft 11, one of the housings 14 being fixed to the shaft so as to be movable therewith, each said housing having connected thereto an orthopedic pin clamp assembly, a lead screw 19 housed within the bore of the shaft 11, and having a thread mating with a thread in the shaft bore, arranged and constructed so that upon rotation of the lead screw 19, the shaft 11 is displaced longitudinally along with the housing 14, to in turn cause an adjustment in the axial distances between the confronting ends of the housing 14 and at least one of the housings 13,15. In the bone transport mode of use, housings 13, 15 remain fixed with respect to the lead screw 19, whilst in the bone lengthening more of use, only one housing 13 is held fixed with respect to the lead screw, the two other housings 14,15 moving, upon adjusted rotation of the lead screw, in unison with the shaft.

9 Claims, 3 Drawing Sheets

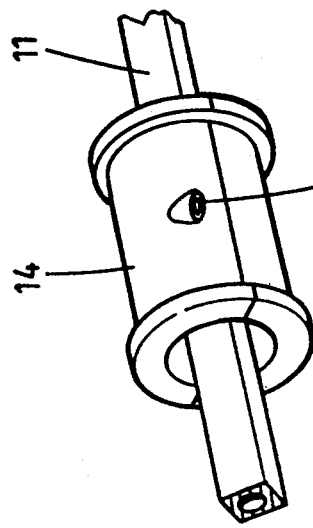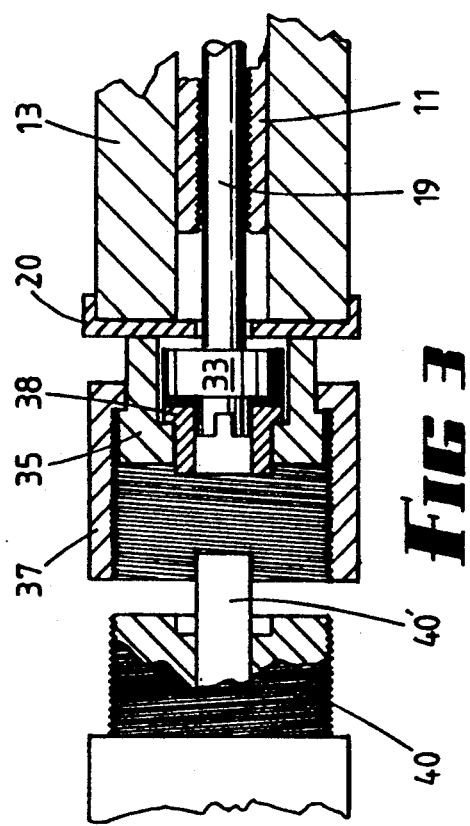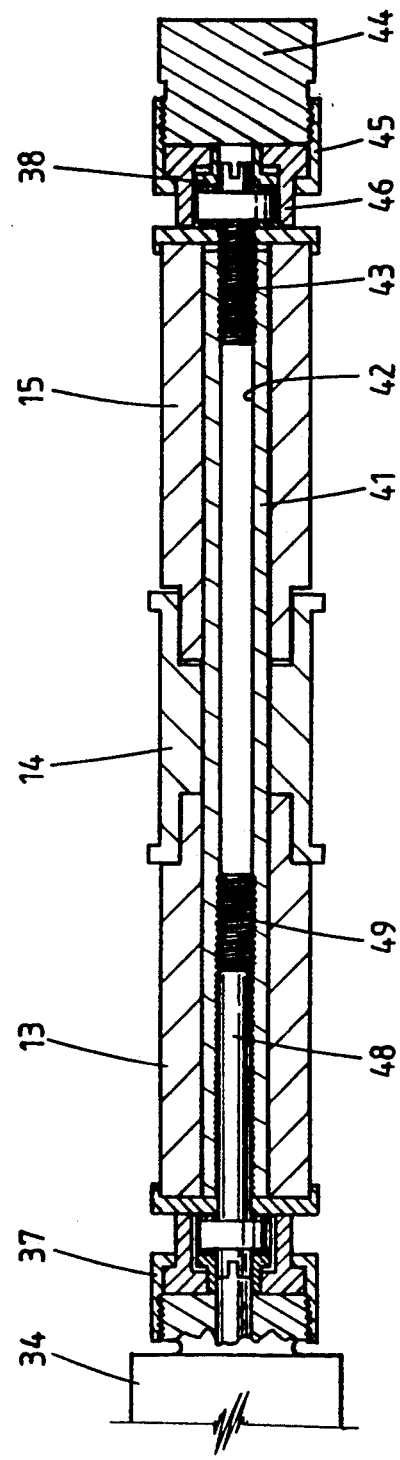

EXTERNAL BONE FIXATION DEVICE

This invention relates to external bone fixation devices used in one treatment of bone fractures and more specifically to a unilateral bone fixation device suitable for use in carrying out bone transport procedures and also bone lengthening procedures.

Gradual bone lengthening by a distraction technique has been used for some years in order to correct a severe limb-length discrepancy. In children, limb lengthening has been achieved by distraction of the growth plate, whilst in adults by distraction through a defect created in the bone, eg a transverse osteotomy, where the bone is cut by the surgeon, and once early bone healing (callus formation) has occurred, lengthening is achieved by distracting the regenerating bone tissue (callus).

Various distracting means have been used over the years, the most commonly used devices being external fixators where each segment of bone is transfixed by pins or wires attached to clamps which are then distracted. Examples of external fixator systems include (i) bilateral frames where fixator bodies or rods are located one on each side of the bone being transfixed, (ii) unilateral frames where only a single fixator body or rod is located to one side of the bone, and (iii) ring fixators where a series of rings are spatially arranged around the limbs so as to form a cylinder, the rings being interconnected by struts.

In acute trauma. or in other conditions, eg tumor resection, bone infection excision, a section of the defective bone may be lost. Bone loss may be addressed by a procedure known as bone transport which is based on the sam®principles as bone lengthening. In bone lengthening, an external fixator device is used to distract two bone fragments away from one another towards the end of the bone, to thereby lengthen the bone, whilst in bone transport, the fixator is used to close a bone defect/gap, this being achieved normally by one fragment of the defective bone, generally the larger fragment, being transected, eg by a transverse osteotomy, followed thereafter by distracting the inner bone fragment of the larger transected fragment towards the defect rather than towards the end of the bone which occurs in bone lengthening. The bone is thereby reconstituted while maintaining the original bone length.

An alternative method of managing a bone defect and which is preferred by some surgeons, is to juxtapose the ends of the defective bone, to thereby shorten same, and thereby promote early bone healing at the juncture of the bone ends, followed thereafter by a transection of the larger bone fragment, eg by a transverse osteotomy, and finally distracting the bone fragment so as to regain the original bone length. The end result of this procedure is identical to that described above but is achieved by different procedural steps. Thus, a surgeon faced with a bone defect may elect to treat same by either one of these two procedures. With the second procedure, namely where the original bone length is shortened, this has usually been a two stage procedure where the defect is first allowed to heal and the bone is subsequently lengthened. Each stage may take several months. It is, however, possible to have the two stages occurring simultaneously, thereby decreasing the total healing time.

Since the above described two different procedures have in the past required the use of different fixators this has necessitated hospitals holding stooks of both—it being left to the surgeon to elect which procedure is to be performed.

As explained in our earlier patent application PCT/AU91/00036 filed Feb. 5, 1991, it is desirable for an external fixation device to be able to provide reliable and efficient dynamisation (both active and passive) in a manner which will promote fracture healing of the bone. In the case of bone transport procedures, dynamisation is preferred at the defect site and may also be required at the site of lengthening after the required length is attained.

The present invention provides further improvements and/or modifications to a fixator of the kind described and illustrated in our aforesaid PCT application, which will render same suitable for both bone transport and bone lengthening procedures.

It is an object of the present invention to provide an improved unilateral external bone fixation device which is of simple construction, of relatively low cost, and which can be readily adapted for carrying out either bone transport or bone lengthening procedures.

It is another object of the present invention to provide improvements to a unilateral external bone fixation device which are designed so that the device has the ability to dynamise (axial loading and/or axial motion), to thereby promote fracture healing, at the defect site of the defective bone either prior to bone lengthening of one of the bone fragments or simultaneously with bone lengthening of one fragment, or by accelerating bone callus formation, at the osteotomy site of the defective bone.

It is a further object of the present invention to provide an improved form of external fixator device which will allow the rate of lengthening of the bone to be easily and accurately controlled.

It is a still further object of the present invention to provide an improved form of bone transport external fixator which can be easily and readily adapted to provide passive fracture stimulation for immobilized patients and also active fracture stimulation once the patient is ambulatory.

It is yet a further object of the present invention to provide an improved form of dynamised external fixation device which, by virtue of its compactness, will permit early patient activity and walking, thereby promoting early return of joint motion and musole function and strength.

Broadly according to this invention therefore, an improved unilateral external bone fixation device having a common central longitudinal axis, comprises a central non-rotatable rigid shaft or rod having a central bore extending therethrough and being longitudinally displaceable along the axis of the device, a plurality of clamp carrier housings each having a central passage extending therethrough, said housings being co-axially supported along the length of the shaft or rod, the shaft or rod slidably engaging and extending through the passages of the housings, one of said housings being fixed to the shaft so as to be movable therewith, each said housing being adapted to support an orthopedic pin clamp assembly for removably securing one or more fixator retainer pins therein, a lead screw or threaded rod housed within tho bore of the shaft or rod and having a thread mating with a thread in the shaft bore, means at one end (the proximal end) of said shaft or rod and co-axial therewith for rotating said lead screw or threaded rod, arranged and constructed so that rotation of said lead screw, imparts longitudinal displacement to said shaft, said displacement simultaneously causing an adjustment in the axial distance between the confronting ends of said one of the housings and at least one of said other housings.

More specifically, there are three clamp carrier housings in co-axially aligned relationship, with the intermediate housing being fixedly secured with the shaft or rod so as to move therewith, the other two end housings when the device is being used for bone transport, being held stationary relative to the lead screw whilst when the device is being used for bone lengthening, only one (proximal) of the end housings is held stationary relative to the screw, the other (distal) end housing being arranged upon rotation of the screw, to move with the intermediate housing in fixed relationship therewith. In this description, the proximal end housing is that which is located adjacent the head end of the lead screw.

For bone transport procedures, the lead screw extends the whole length of the shaft or rod and has its ends journalled for rotation in respective bearing means supported at opposite ends of the fixator device, whilst for bone lengthening, the long lead screw can be replaced by a relatively short lead screw which projects inwardly from the proximal end of the shaft by a distance which is less than the length of the shaft or rod.

Preferably the shaft or rod is polygonally shaped most preferably rectangular or square, and has a cylindrical bore extending centrally therethrough.

Preferably each of the clamp carrier housings has an outer cylindrical wall and a square or rectangular bore extending therethrough for snugly receiving the shaft or rod, whilst each of the pin clamp assemblies has a cylindrical connector sleeve releasably affixed to a respective said housing, the connector sleeve when thus released, being rotatable relative to its respective housing.

In the embodiment of the invention applicable to bone transport procedure where the original bone length is maintained, the device comprises a proximal clamp carrier end housing, an intermediate housing and a distal end housing, said intermediate housing being fixedly secured to said shaft or rod so as to move therewith, each said end housing and said shaft being axially slidable relative to one another, the adjusted rotation of the lead screw causing the shaft to be longitudinally displaced with respect to said end housings to in turn vary the positions of the end housings relative to the intermediate housing, the distance, however, between the two end housings remaining fixed.

In the embodiment of the invention applicable to bone lengthening procedure where the bone is initially shortened, the intermediate housing and one of the end housings are held in fixed relationship and move in unison with the shaft which is displaced along the lead screw when the latter is rotated, the other of the end housings remaining stationary with respect to the lead screw.

According to another aspect of the present invention, the fixator of this invention can be readily and quickly adapted to operate in the bone lengthening mode without the need to replace the long lead screw with the relatively short lead screw. In this embodiment, the distal end housing has coaxially attached thereto removable locking means which is adaptable so that in a bone transport mode of use, the distal end housing, during rotation of the screw, remains fixed with respect to the lead screw, and therefore at a constant distance from the proximal end housing, with only the intermediate housing moving relative to the lead screw, whilst in a leg lengthening mode of use, the locking means permits the distal end housing to move, upon rotation of the lead screw, in unison with the intermediate housing, such movement being relative to the proximal end housing which remains stationary with respect to the lead screw. In each instance, of course, the shaft is displaced longitudinally.

Preferably, the locking means comprises a tubular locking sleeve threadably engaging the projecting distal end of the screw, the locking sleeve, when the fixator is in its bone transport mode of use, being arranged to rotate simultaneously with the screw, whilst when the fixator is in its leg lengthening mode of use, the sleeve is locked against rotational movement and the screw rotates within it.

In a particularly preferred embodiment, the invention includes actuating means for producing repetitively relative dynamic axial movement between one or both of the end housings and the shaft, and in turn relative limited axial movement between the pin clamp assemblies carried by the housings, said actuating means being co-axially attached to one or both ends of said device.

In some instances, relative dynamic axial movement between the end housings is desirable. The actuating means may comprise a co-axially attached DC motor, particularly in the case where an immobile patient requires bone fracture exercise or passive stimulation. Alternatively the actuating means may comprise a calibrated spring axial loading device in the case where the patient is ambulatory. In both instances, the actuating means provides dynamisation (axial movement or loading) at the defect site (and also at the osteotomy site) to enhance and promote rapid healing.

It will be appreciated by those skilled in the art that where the device is being used for bone transport procedures, it is advantageous to be able to provide for dynamic axial loading and/or movement at the osteotomy site as well as the defect or docking site. The present invention allows this to be achieved in a very simple and effective manner, eg by attaching appropriate removable end fittings to the ends of the device, which permit limited relative axial movements to occur between the end housings and the shaft.

The arrangement of the pin clamp assemblies and the pin clamps are identical to those described and illustrated in our aforesaid co-pending PCT application, the contents of which are incorporated herein by reference.

In order to more fully explain the invention several embodiments are described hereunder in some further detail with reference and as illustrated in the accompanying drawings wherein FIG. 1 is a plan view of an improved fixator device according to a first embodiment of the invention, applied to a defective bone of a patient;

FIG. 3 is a fragmentary sectional view of the device shown in FIG. 2, with the proximal end housing shown in its dynamising mode, wherein it can move axially relative to the shaft, together with an axial loading fitting for fitment to the housing;

FIG. 4 is a longitudinal sectional view taken through the main body of a fixator device according to a second embodiment of the invention;

FIG. 5 is a fragmentary perspective view of the intermediate clamp carrier housing shown in FIGS. 2 and 4;

Figure 1:
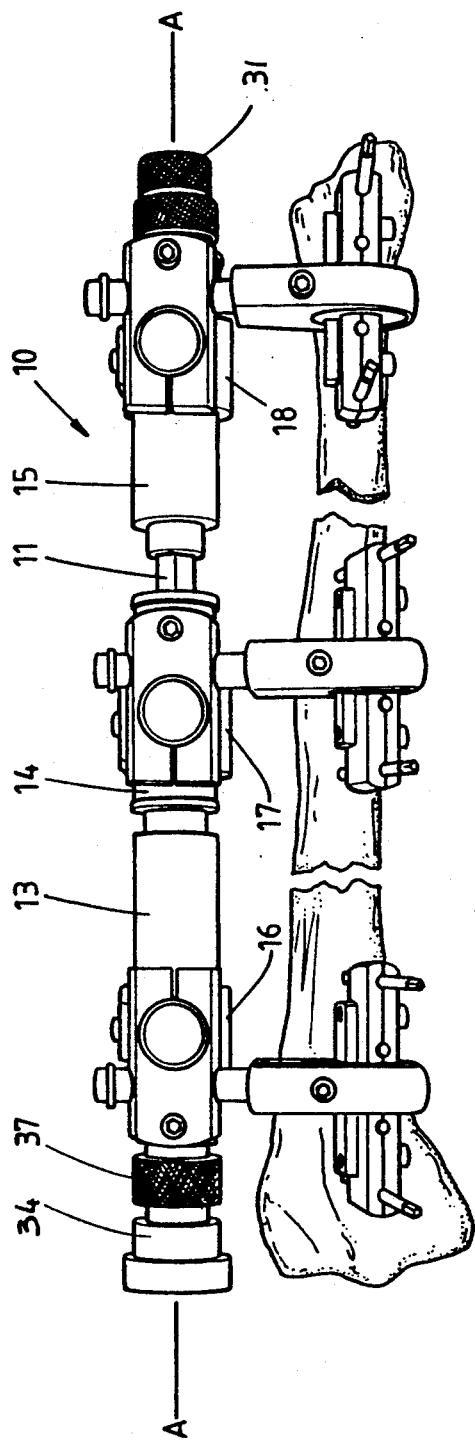
Figure 2:
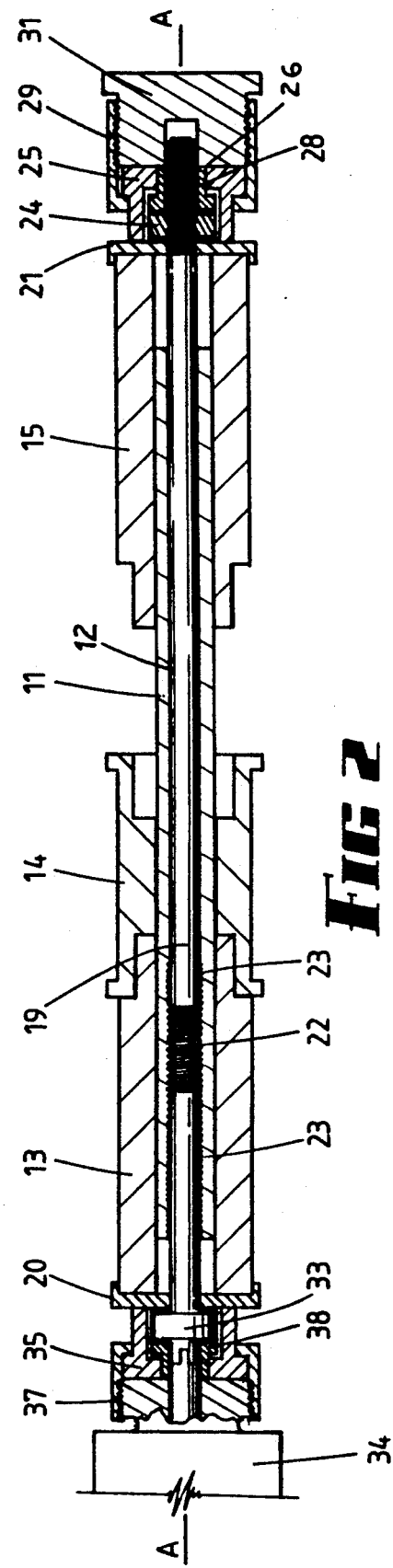
FIG. 2 is a longitudinal sectional view taken through the fixator device shown in FIG. 1 (but without the clamp carriers), wherein the end housings are looked against axial movement with respect to the lead screw.

In the embodiment shown in FIGS. 1 and 2, there is shown an improved external fixator device 10 comprising a rigid, non-rotating, square or rectangular shaft or rod 11 which is co-axial with the longitudinal axis "A" of the device 10 and extends longitudinally thereof, the shaft 11 having a cylindrical bore 12 extending therethrough. The shaft 11 non-rotatably supports a plurality of clamp carrier housings 13, 14 and 15 in co-axial relationship, each having an outer cylindrical wall and a non-circular bore therethrough. As shown in FIG. 1, the housings 13, 14 and 15 have co-axially attached thereto adjustable connector sleeves 16, 17, 18 respectively, which in turn support respective orthopedic pin clamp assemblies comprising pin clamps in which are removably secured one or more fixator retainer pins, the pins being inserted into respective fragments of the defective bone. The connectors, pin clamps and retainer pins are essentially in accord with the constructional details described in our earlier PCT Application No PCT/AU91/00036, and do not form part of the present invention.

In accordance with a feature of the present invention, there is provided a lead screw 19 which is threadably received within the bore 12 of the shaft 11 and extends therethrough. In this embodiment, the lead screw 19 projects from each end of the device 10 through openings in end plates 20, 21 attached to the outer ends of the housings 13, 15 respectively. The screw 19 has a threaded portion 22 which threadably engages a threaded portion 23 of the bore 12 at the proximal end of the shaft 11. The distal end of the lead screw 19 is also threaded and threadably receives a nut 24 which is housed in a co-axial extension body portion 25 of housing 15, the body portion 25 being rigidly fixed to the end of the distal end housing 15 by means of fixing screws (not shown). The portion 25 has a central passage through which extends the projecting end of the lead screw 19, the passage terminating in a small diameter opening 26 which is sized so that an annular clearance exists between the lead screw 19 and the peripheral wall of the opening 26. An axially movable dynamising spacer 28 is slidably carried on the end of the screw 19 and snugly fits into the annular clearance. A joining sleeve 29 is slidably retained on the portion 25 and is internally threaded for receiving an end closure cap 31 which, when fully tightened, bears against the radial end walls of the housing portion 25 and spacer 28 to thereby lock same against axial movement. Thrust washers are located on either side of the nut 24.

The proximal end of the lead screw 19 has an enlarged head 33 which is keyed to a manually rotatable fitting 34 so that as the fitting 34 is manually rotated, the lead screw 19 is rotated simultaneously, rotation of the lead screw in turn effecting longitudinal to and fro movement of the shaft 11. The head 33 of the lead screw is housed in an extension portion 35 of housing 13, the portion 35 being fixedly mounted to the proximal end housing 13 by securing screws (not shown). A knurled collar 37 slidably retained on portion 35, is used to releasably couple the fitting 34 to the end housing 13. When fully tightened, the fitting 34 bears against the portion 35 and spacer 38 (identical to spacer 28) to thereby lock the housing 13 against relative axial movement with respect to the screw 19.

The intermediate clamp carrier housing 14 is rigidly fixed to the shaft 11 and moves therewith, whilst each of the housings 13, 15 remain stationary relative to one another upon rotation of the screw 19. This arrangement of course allows the fixator 10 to be used to close a bone defect/gap by virtue of the movement of the intermediate housing 14 which has its pins inserted into an inner bone fragment of the defective bone (refer FIG. 1), such movement of the housing 14 towards the housing 15 causing the inner bone fragment to be distracted towards the defect site.

As shown in FIG. 5, the intermediate clamp carrier housing 14 can be formed in two halves and simply frictionally clamped onto the shaft 11 by means of clamping screws 39. Alternatively the housing can be formed as a unitary moulding slidably fitted to the shaft 11 and releasably locked thereto.

Referring to FIG. 3, the fixator device is shown with the proximal end housing 13 in its dynamising mode, the end fitting 34 having been removed. In this mode, a dynamising gap eg 1 mm exists between the head end 33 of the screw 19 and the end plate 20 of housing 13. An axial loading unit 40, similar to that described in our co-pending PCT Application No PCT/AU91/00036, be threadably attached to the collar 37, with its central stem 40' making pressure contact against the head 33 of the screw. A resilient compression spring (not shown) is housed within the unit 40 which co-acts with the screw 19 and in turn the shaft 11, to provide an adjustable spring resistance to bodily axial movement of the housing 13 relative to the shaft 11.

In order to dynamise the other end housing 15, end cap 31 is removed and replaced by a fitting similar to fitting 40, and the dynamisation gap existing between the radially out-turned flange on spacer 28 and the radially inwardly directed flange on the fixed extension portion 25, allows the housing 15 to undergo the required excursion during either dynamic axial loading or dynamic axial motion.

Referring to FIG. 4 of the drawings, a second embodiment of an external fixator of this invention is shown, and which comprises identical clamp carrier housings 13, 14 and 15, and identical pin clamp assemblies and retainer pins removably secured therein. However, in this embodiment, the bore 42 which extends through the rectangular rigid shaft 41 has a threaded end portion at its distal end which threadably receives a connecting screw 43. The head of the screw 43 bears against an inner radial wall of a co-axial, threaded end fitting 44 which threadably engages nut 45 which in turn is slidably supported by adaptor 46 secured by fixing screws to the housing 15. Thus, during distraction, the housing 15 is fixed with respect to the shaft 41, and moves therewith. During dynamisation, the fitting 44 is removed to allow the screw 43 and the shaft 41 to move axially together relative to the housing 15. Normally, a dynamisation gap of approximately 1 mm is provided, by means of spacer 38, to permit dynamic axial movement of the housing 15.

The lead screw 48 is short relative to the lead screw 19 of the first embodiment, and is provided with a threaded inner end portion 49 which threadably engages a threaded portion of the bore 42 of the shaft 41, the threaded bore portion being formed by a drilling and tapping operation. The fittings at the proximal end of the fixator device are similar to those described in the first embodiment and co-operate together, so that when in the looked mode, the housing 13 remains stationary relative to the screw 48 during rotation thereof.

The intermediate clamp carrier housing 14 is fixedly clamped to the shaft 41 and is arranged to move therewith; however, the distal end housing 15, in contradistinction to the first embodiment, is fixed with respect to the shaft 41, the arrangement being such that upon rotation of the lead screw 48, the shaft 41, along with the housings 14, 15, are displaced longitudinally in a fixed orientation along the axis of the device, the housing 13 remaining stationary. This mechanism is suitable for carrying out bone treatment procedure where the defective bone is initially shortened so as to close the bone defect, whereafter the larger bone fragment is transected eg by a transverse osteotomy, and then distracted to regain the original bone length. In this instance, the pin clamp assemblies supported by housings 14 and 15 have their retainer pins respectively transfixed to the inner bone fragment and the outer bone fragment remote from the closed defect. This procedure will be readily understood by those skilled in the art.

Figure 6:
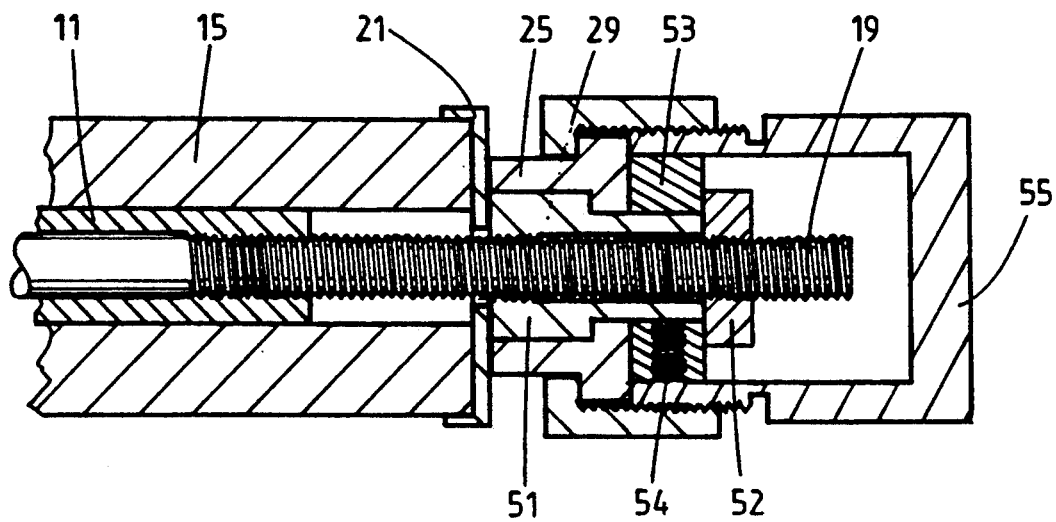
FIG. 6 is a fragmentary sectional view of the distal end housing of the fixator shown in FIG. 1, having a modified end fitting which is shown in the bone transport mode of use; whilst
Figure 7:
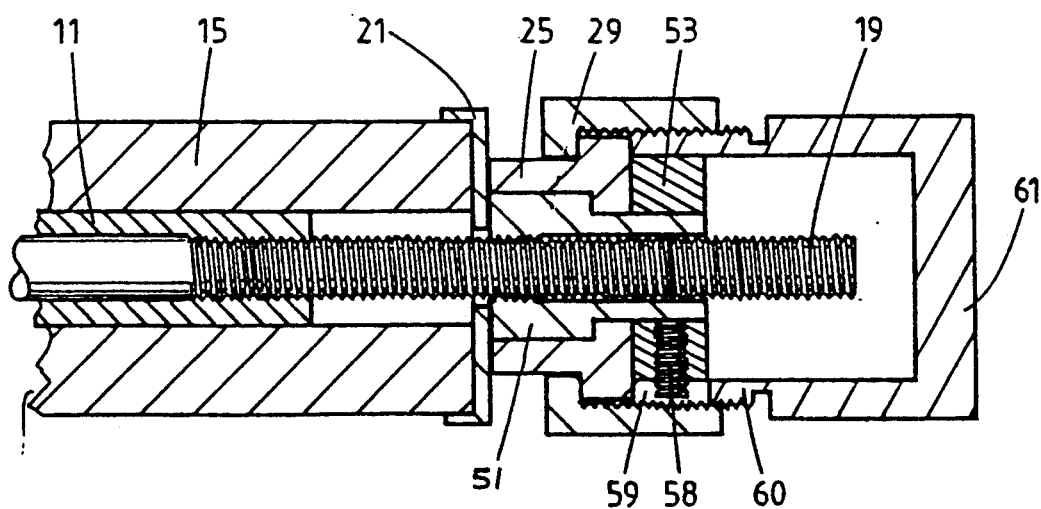
FIG. 7 is a view similar to that of FIG. 6 which shows a further end fitting attached to the distal end of the screw when the fixator is in its bone lengthening mode of use.

Referring now to FIG. 6 of the drawings, the fixator of FIG. 1 is modified in that the distal end housing 15 is retained on the projecting end of the lead screw 19 by means of an elongate locking sleeve 51 which is screwed onto the lead screw 19 and is rotatably housed within co-axial extension body portion 25, the sleeve 51 in turn being held in place by a lo 52. An annular manual setting knob 53 is slidably supported on a tail portion of sleeve 51 and is locked thereon by means of grub screw 54. An end cap 55 is threadably received within the threaded bore of joining sleeve 29 and closes off the distal end of the fixator. FIG. 6 shows the fixator in a bone transport mode of use, with the sleeve 51 being looked to the lead screw 19 by nut 52 and being made to revolve therewith. In this condition, the position of housing 15 is controlled by the lead screw 19 and remains fixed with respect thereto. With the housing 13 also being fixed with respect to the screw 19, the end to end distance between the housings 13, 15 remains constant with only the axial distance between the confronting ends of the housings 13, 14, 15 being altered, due to the movement of housing 14 fast with shaft 11. Referring to FIG. 7, the connection on the end of the screw 19 is arranged so that the fixator can be used for bone lengthening without the need to replace the lead screw 19. This is achieved by removing the end cap 55, the lock nut 52 and also the grub screw 54 (shown in FIG. 6). A longer grub screw 58 is screwed into the knob 53, the grub screw 58 having a projecting outer end portion which locates in a slot 59 formed in the skirt 60 of end cap 61 which is threadably connected to joining sleeve 29. With screw 58 lightened and the cap 61 fitted, the knob 53 and in turn the sleeve 51 are prevented from turning as the screw 19 is rotated. As the pitch on the lead screw 19 is the same at both ends, the sliding shaft 11 together with the intermediate housing 14 and the end housing 15 remain in a fixed orientation and all move simultaneously relative to the end housing 13 upon adjusted rotation of the lead screw 19.

In each embodiment, the lengthening of the defective bone in either of the aforementioned bone transport procedures can be controlled through a manual screw tightening a device or a motorised device co-axially attached to the knurled collar 37 to drivingly couple with the extension portion 35 and the shaft 11. A manual screw tightening device enables a surgeon to manually adjust the rate of distraction, eg 1 mm once daily or in divided increments, eg 4×¼ mm daily, whilst the motorised device enables a predetermined lengthening rate to be achieved, with the motor being run continuously or intermittently.

The present invention will allow dynamisation to occur at the fracture site, either by dynamised axial motion through a coaxially attached motor, eg when a patient is bed bound, or by dynamic axial loading using a calibrated spring loaded device (as described in our earlier co-pending PCT Application No. PCT/AU91/00036 ), in each instance the dynamisation being achieved by repetitive oscillating movement occurring between the housings 13, 14, 15 and in turn their pin clamp assemblies, such movement being possible by virtue of the sliding engagement of the shafts 11, 41 in the bores of the housings 13, 15. For axial dynamic loading to occur with the fixator shown in FIG. 4, the end cap 44 will need to be removed.

A brief consideration of the above described embodiments will indicate that the invention provides an improved form of external bone fixation device which is especially suited for carrying out bone transport procedures, although it should be appreciated that the invention may be adapted for use in conventional bone lengthening procedures where two bone fragments are distracted from one another towards the respective ends of the bone. The fixator of the present invention is of extremely simple construction and permits simple and ready attachment of an actuating device for producing dynamisation at the defect site, in a compact manner.

We claim:

1. An improved unilateral external bone fixation device having a central longitudinal axis, comprising a central non-rotatable rigid shaft or rod having a central bore extending therethrough and being longitudinally displaceable along the axis of the device, first, second and third clamp carrier housings co-axially supported along the length of the shaft or rod, the second housing being the intermediate one of said housings and being fixed to the shaft so as to be movable therewith, each said housing being adapted to support an orthopedic pin clamp assembly for removably securing one or more fixator retainer pins therein, a lead screw housed within the bore of the shaft or rod and having a thread mating with a thread in the shaft bore, said lead screw being rotatable from one end thereof, and adjustment means for adjusting the axial distance between confronting ends of said intermediate housing and at least one of the other housings, said adjustment means arranged and constructed so that rotation of the lead screw imparts longitudinal displacement to said shaft and also to said intermediate housing fast therewith relative to said at least one of the other housings.

2. An improved unilateral external bone fixation device according to claim 1 wherein the first housing is a proximal end housing, and the third housing is a distal end housing, said adjustment means including each one of said end housings having an outer end co-axially attached to a fitting, the fittings releasably locking said end housings in a fixed relationship with respect to the lead screw, so that when said lead screw is rotated, the respective distances between the confronting ends of the intermediate housing the end housings are adjusted, with the end housings remaining a constant distance apart.

3. An improved unilateral external bone fixation device according to claim 2 wherein said lead screw has a length greater than the length of said shaft and extends completely through said housings and projects beyond the outer end of said distal end housing, said proximal end housing fitting being detachably coupled with respect to the proximal end housing and being drivingly connected to said one end of the lead screw for rotating the lead screw.

4. An improved unilateral external bone fixation device according to claim 2 wherein the shaft or rod is rectangular or square and has a cylindrical bore extending centrally therethrough.

5. An improved unilateral external bone fixation device according to claim 4 wherein each of the housings has an outer cylindrical wall and a square or rectangular bore extending therethrough for snugly receiving the shaft or rod.

6. An improved unilateral external bone fixation device according to claim 2 wherein said fitting associated with at least one of said end housings, when in a released condition, permits at least one of said end housings to undergo limited reciprocal axial sliding movement relative to said lead screw to thereby enable dynamisation to occur at a defect site in the bone being treated.

7. An improved unilateral external bone fixation device according to claim 1 wherein said lead screw has a length which is short relative to the length of said shaft, said adjustment means arranged and constructed so that the rotation of the lead screw causes the shaft to be longitudinally displaced with respect to only one of said first and third housings, with said shaft, the intermediate housing and the other of said first and third housings being held in fixed relationship with one another whereby both the intermediate housing and the other of said first and third move in unison wit the shaft relative to said one housing.

8. An improved unilateral external bone fixation device according to claim 1 wherein the first housing is a proximal end housing, and the third housing is a distal end housing, said adjustment means including said proximal end housing having an outer end attached to a first fitting, the first fitting locking said proximal end housing in a fixed relationship with respect to the lead screw, said distal end housing having an outer end being coaxially attached to a second fitting, the second fitting permitting the distal end housing to move simultaneously with said shaft relative to said lead screw, arranged so that when said lead screw is rotated, said intermediate housing and said distal end housing moving in unison, such movement being relative to said proximal end housing, whereby to establish a lengthening of the bone being treated.

9. An improved unilateral external bone fixation device according to claim 8 wherein said lead screw has a length which is short relative to the length of said shaft, said proximal end housing fitting being detachably coupled with respect to the proximal end housing and being drivingly connected to said one end of the lead screw for rotating the lead screw.

* * * * *